(12) United States Patent
Kruk (10) Patent No.: US 10,213,211 B2
(45) Date of Patent: Feb. 26, 2019

(54) MEDICAL DEVICE AND METHODS FOR BLOOD VESSEL COMPRESSION

(71) Applicant: INSTYTUT KARDIOLOGII, Warsaw (PL)

(72) Inventor: Mariusz Kruk, Sulejowek (PL)

(73) Assignee: INSTYTUT KARDIOLOGII, Warsaw (PL)

( * ) Notice: Subject to any disclaimer, the term of this patent is extended or adjusted under 35 U.S.C. 154(b) by 1141 days.

(21) Appl. No.: 14/354,890

(22) PCT Filed: Oct. 28, 2012

(86) PCT No.: PCT/EP2012/071323
§ 371 (c)(1),
(2) Date: Apr. 28, 2014

(87) PCT Pub. No.: WO2013/060883
PCT Pub. Date: May 2, 2013

(65) Prior Publication Data
US 2014/0288590 A1     Sep. 25, 2014

Related U.S. Application Data

(60) Provisional application No. 61/555,477, filed on Nov. 4, 2011.

(30) Foreign Application Priority Data

Oct. 28, 2011   (PL) .......................................... 96805

(51) Int. Cl.
*A61B 17/132*     (2006.01)
*A61B 17/00*      (2006.01)
(Continued)

(52) U.S. Cl.
CPC .............................. *A61B 17/1325* (2013.01); *A61B 2017/00889* (2013.01); *A61B 2017/00893* (2013.01);
(Continued)

(58) Field of Classification Search
CPC .............. A61B 17/132; A61B 17/1325; A61B 2017/00889; A61B 2017/00893;
(Continued)

(56) References Cited

U.S. PATENT DOCUMENTS 3,954,109 A   5/1976  Patel
4,196,735 A   4/1980  Ayer
(Continued)

FOREIGN PATENT DOCUMENTS

DE      10135350 A1    2/2003
EP       1358851 A1   11/2003
(Continued)

*Primary Examiner* — Wade Miles
*Assistant Examiner* — George J Ulsh
(74) *Attorney, Agent, or Firm* — Browdy and Neimark, PLLC (57) ABSTRACT

The invention relates to a medical device and method for applying pressure onto a patient's limb, especially at a blood vessel or a wound site, in order to achieve local hemostasis. The device comprises a body (1) for blood vessel compression, holding element (2) for attaching the body (1) to a patient's limb, a fastening means (3) for holding the device in a desirable position, wherein the body (1) has a first compression area (1a) which is situated at the outer surface of the body (1), at least one second compression area (1b) through which the body (1) is pressed with a holding element (2), a third compression area (1c) for compression control during application of the device, and wherein the holding element (2) is guided over the first compression area (1a), when the device is attached to the patient's limb.

37 Claims, 9 Drawing Sheets

(51) Int. Cl.
*A61B 17/12* (2006.01)
*A61B 90/00* (2016.01)
(52) U.S. Cl.
CPC ............... *A61B 2017/00902* (2013.01); *A61B 2017/12004* (2013.01); *A61B 2090/064* (2016.02); *F04C 2270/0421* (2013.01)
(58) Field of Classification Search
CPC .... A61B 2017/00902; A61B 2090/064; A61B 2017/12004; F04C 2270/0421
See application file for complete search history.

(56) References Cited

U.S. PATENT DOCUMENTS

| | | | | |
|---|---|---|---|---|
| 4,243,039 | A * | 1/1981 | Aginsky | A61B 17/1327 |
| | | | | 606/203 |
| 4,297,996 | A * | 11/1981 | Uriza | A61B 17/1322 |
| | | | | 602/53 |
| 5,269,803 | A | 12/1993 | Geary | |
| 5,507,721 | A | 4/1996 | Shippert | |
| 5,797,862 | A * | 8/1998 | Lamont | A43B 5/0415 |
| | | | | 36/154 |
| 6,752,820 | B1 | 6/2004 | Hafemann | |
| 6,899,720 | B1 | 5/2005 | McMillan | |
| 2003/0114881 | A1 | 6/2003 | Stalemark | |
| 2005/0165445 | A1 * | 7/2005 | Buckman | A61F 13/00 |
| | | | | 606/213 |
| 2008/0119774 | A1 * | 5/2008 | Paasche | A61F 13/00021 |
| | | | | 602/53 |
| 2008/0188788 | A1 * | 8/2008 | Serola, D.C. | A61B 17/1325 |
| | | | | 602/75 |
| 2008/0312682 | A1 | 12/2008 | Shams et al. | |
| 2010/0280541 | A1 * | 11/2010 | Lampropoulos | A61B 17/1325 |
| | | | | 606/203 |
| 2011/0125112 | A1 * | 5/2011 | Bainbridge | A61B 46/27 |
| | | | | 604/304 |
| 2012/0150215 | A1 * | 6/2012 | Donald | A61B 17/1325 |
| | | | | 606/203 |

FOREIGN PATENT DOCUMENTS

| | | | | |
|---|---|---|---|---|
| EP | 1382306 | A | 1/2004 | |
| EP | 2193751 | | 6/2010 | |
| EP | 2245998 | A1 | 11/2010 | |
| JP | 9187461 | A | 7/1997 | |
| JP | 2004187955 | A1 | 7/2004 | |
| JP | 2005511237 | A | 4/2005 | |
| JP | 2009508613 | A | 3/2009 | |
| JP | 2009291380A | A1 | 12/2009 | |
| WO | 96/25110 | A1 | 8/1996 | |
| WO | 97/04821 | A2 | 2/1997 | |
| WO | 97/05838 | A1 | 2/1997 | |
| WO | WO 2007075515 | A2 * | 7/2007 | ......... A61B 17/1325 |
| WO | 2011/012805 | A1 | 2/2011 | |
| WO | 2012129146 | A2 | 9/2012 | |

* cited by examiner

MEDICAL DEVICE AND METHODS FOR BLOOD VESSEL COMPRESSION

TECHNICAL FIELD

The invention relates, in general, to a medical device and method for applying pressure onto a patient's limb, especially at a blood vessel or a wound site, in order to achieve local hemostasis. More particularly, the device of the invention is employed in invasive cardiology and radiology, during the removal of the vascular sheath after heart catheterization (coronary angiography) or after other procedures and interventions that require a vascular access port for intravascular procedures. The device allows for blocking of the outflow of blood which accompanies the removal of the vascular sheath.

PRIOR ART

The currently known technical solutions aimed at achieving the proper haemostasis often require that a series of consecutive actions is performed one after another, often by at least two persons, mostly a doctor and a nurse, working in cooperation. As part of the actions, a band is put around the patient's arm, next the band is fastened at the wrist, pressure is applied to the insertion site while the cannula is being removed, and finally the band is secured in such a way as to preserve the proper level of pressure at the insertion site.

Several devices that are available on the market aim to provide hemostatic control and simplify the above described procedure. One of the devices marked under a name Radistop™ (RADI, Uppsala, Sweden), which has been described in WO96/25110, comprises an elongated compression element and a pressure distribution and support plate held on an opposite side of the risk with straps.

There are also devices that employ inflatable balloons, which are filled with air or other fluid to apply pressure on the radial artery. These devices include a TR Band™ (Terumo, Japan), described in EP1382306 and EP2245998, and a radial artery compression device described in WO2012/129146.

The radial compression devices known in the prior art either do not provide the sufficient level of pressure control when they are applied or have a very complex construction and require pressure control means or additional devices, such as inflator syringes, to be fully functional.

SUMMARY OF THE INVENTION

The object of the present invention is to provide such a medical device that has a very simple construction and is useful for blood vessel compression. The device of the invention protects the patient from bleeding and simultaneously facilitates the work of the medical staff. The invention is aimed at limiting a number of actions required to secure the compression band and keep the desired level of pressure at the insertion or wound site. Another goal is to eliminate the assistance of additional medical personnel or the use of additional equipment currently required during the removal of a vascular sheath. In addition, the invention is to ensure a convenient access to the insertion or wound site from any direction, while preserving a free outflow of venous blood from the limb.

The invention provides an improved arterial compression band employed to compress radial artery in an easier, faster and clinically more efficient way. Its simple construction ensures both proper pressure control and ease of application.

The medical device of the invention comprises a body for blood vessel compression, holding element for attaching the body to a patient's limb at a contact site of the body with the patient's limb, a fastening means for holding the device in a desirable position on the patient's limb wherein the body has
- a first compression area for applying the compression force to the blood vessel at the contact site situated within the first compression area, said first compression area being situated at the outer surface of the body,
- at least one second compression area through which the body is pressed with a holding element against patient's limb,
- a third compression area adapted to be pressed manually for compression control during application of the device onto the patient's limb, and the holding element is guided over the first compression area, when the device is attached to the patient's limb.

In preferred embodiment the first compression area, the second compression area and the third compression area are situated coaxially with respect to each other and the second compression area and the third compression area are situated over the first compression area. Thereby the greater stability of the device is provided.

Another preferred feature of the device of the invention is that the third compression area is a cavity in the body or an opening within the body, which facilitates a better grip of the device during application.

In the second embodiment, a medical device of the invention comprises a body for blood vessel compression, holding element for attaching the body to a patient's limb at a contact site of the body with the patient's limb, a fastening means for holding the device in a desirable position on the patient's limb wherein the body has
- a first compression area for applying the compression force to the blood vessel at the contact site situated within the first compression area, said first compression area being situated at the outer surface of the body,
- at least one second compression area through which the body is pressed with a holding element against patient's limb,
- a third compression area adapted to be pressed manually for compression control during application of the device onto the patient's limb, and is hollow and the third compression area is situated inside the body.

The preferred features of both embodiments of the invention are presented below.

In the preferred embodiment the first compression area has a convex shape. This preferred shape of the first compression area limits the contact of the body with the patient's limb, thus maintaining blood flow through surrounding vessels and limiting pressure on the neighboring nerves. Also preferably the body of the device of the invention has an elongated shape, thus providing the compression on the desired segment of the blood vessel. In case of the radial artery compression after vascular sheath removal, the elongated shape of the body ensures that artery segments of sufficient length on both sides of the insertion site (i.e. the post puncture site) are pressed by said body.

In another preferred embodiment, the body has a cylindrical-like shape and more preferably a longitudinal cross section of the body is a parallelogram and a transverse cross section of the body is an ellipse. In another preferred embodiment, the body has a cylindrical-like shape with beveled endings and more preferably a longitudinal cross section of the body is a trapezoid and a transverse cross section of the body is an ellipse. The beveled ending of the cylindrical-like body render the third compression area more accessible to be pressed.

The medical device of the invention can be used for compression of a large blood vessel, such as a femoral artery. To accommodate greater compression forces the body of the device of the invention has preferably an ellipsoid-like shape and more preferably an ellipsoid shape with at least one truncated ending.

In yet another preferred embodiment the body of the medical device of the invention has two separate second compression areas. More preferably, it has a halfpipe-like shape (i.e. the body has a u-shaped transverse cross section).

The third compression area of the device of the invention is preferably adapted to be pressed with a thumb. That is the size, shape and location of the third compression area relative to the body of the medical device is such that the body of the device can be pressed against the patient's limb with a thumb. Alternatively, when the medical device is used for compression of large blood vessels, such as a femoral artery, the third compression area of the device of the invention is preferably adapted to be pressed with four fingers or with the entire palm.

In preferred embodiment the distance between the first compression area and the third compression area is smaller than the distance between the first compression area and the second compression area. In an alternative preferred embodiment the distance between the first compression area and the second compression area is smaller than the distance between the first compression area and the third compression area.

The medical device is preferably equipped with the elastic pad that is attached to the first compression area. This elastic pad increases the comfort of the patient during compression. In particular, it provides more local compression and additional comfort while withdrawing the sheath. More preferably, the elastic pad is detachably attached to allow exchanging of the pad. Thus the medical device can be used repeatedly provided that the disposable pad is exchanged between the procedures. To ensure better attachment of the pad to the body, it can be preferably attached in a recess or cavity situated in the first compression area.

In the most preferred embodiment the elastic pad attached to the first compression area is made of a heat activated material, which preferably softens at the temperature around the body temperature. Thus, when the device is applied to the patient's limb the pad softens gradually as it is warmed up to the body temperature. That way the pressure exerted onto the patient's limb decreases with the time during the application of the device, and the blood flow in the compressed blood vessel is progressively increased without intervention of the medical staff or manual manipulation of the device. Most preferably the elastic pad is made of rubber, silicon or foam materials.

The elastic pad preferably has an elongated shape and is attached alongside of the body. More preferably, the elastic pad extends over the edges of the body, thus increasing the comfort of the patient.

In another most preferable embodiment the holding element is attached to the body in the proximity of the first compression area. This configuration of the holding element relative to the body stabilizes the entire device on the patient's limb during use and prevents accidental change in positioning of the device.

In preferred embodiment the holding element has an inner surface for contacting at least partially with a patient's limb and outer surface situated on the opposite side of the holding element. Also preferably, the length of the holding element is sufficient to be wrapped around the patient's limb and the body at least once.

Other preferred feature is that the fastening means is situated on the holding element. In addition, the fastening means preferably consists of a first part and a second part. More preferably, the first part of the fastening means is situated on the inner surface of the holding element. Even more preferably, the second part of the fastening means is situated on the outer surface of the holding element. The most preferred fastening means is a hook and loop fastener, such as Velcro®. However, other fastening means can be used, for example buckles, preferably tightening buckles, hooks, snap fasteners or adhesives.

In preferred embodiment the inner surface of the holding element is coated with non-skid layer or the entire holding element is made of a non-skid material. This feature stabilizes the device on the patient's limb during use and prevents accidental displacement of the device.

The inner surface of the holding element is preferably equipped, at least partially, with features that increase the patient's comfort during the use and decrease the compression in the areas of the limb, where compression is not desired (for example, in parts of the limb other than the selective blood vessel area). These features are preferably selected from protrusions, openings and recesses. The most preferably, the holding element is equipped at least partially with protrusions.

In preferred embodiment the body is equipped with at least one guiding means for positioning holding element. This feature further stabilizes the device on the patient's limb as it prevents the holding element from skidding from the body during the use and also facilitates the application of the device on the patient's limb.

In an alternative preferred embodiment, the body of the medical device of the invention further comprises a tracking element, which provides a gap for upholding the holding element. Preferably, when the tracking element is present the third compression area is situated on the tracking element and said tracking element is in the proximity of the second compression area from which it is separated by the gap for upholding the holding element. Alternatively, the third compression area is situated directly on the body and the body is equipped with an anchoring element, preferably a hook for hooking up the holding element.

In still other preferred embodiment the holding element has a scale for indicating a position of the holding element, which enables control of compression force applied to the blood vessel. Once the device is applied to the patient's limb, the compression force is applied by the body, which is pressed against the patient's limb by the holding element. Therefore the compression force is changed by altering the positioning of the holding element. Consequently the scale is useful in regulating the compression force.

In another preferred embodiment the body is equipped with adjusting means for adjusting dimensions of the body and thus controlling the compression force applied to the blood vessel. More preferably, a cross-section size of the body is adjustable for controlling the compression force applied to the blood vessel. This feature enables control of the pressure without changing the position of the holding element. This adjustment of the cross-section of the body is preferably implemented by a disruption in the surface area of the body. When a body has a shape of a tube, a break in the longitudinal direction of the tube is used to control the dimension of the body. By pressing the walls of the tube in one direction the dimension of the cross section of the tube is decreased and by pressing the walls in the opposite direction the dimension of the cross section of the tube is increased. The mechanism for adjusting of the cross section of the body needs to prevent accidental changes in the body dimensions. In preferred embodiment, the break in the tube wall is equipped with a rack/teeth element. Preferably the rack/teeth element is in the shape of leaned sawteeth. This is to prevent accidental slippage of the upper versus lower parts of the tube wall. By pressing the tube wall at the break site, one part of the wall is shifted relatively to the other. More preferably, the shift of the tube walls at the break site is blocked with by winglets. When the parts of the ring are in the extreme shift, further movement is prevented by the winglets pressing against each other. Moreover, by pressing the winglets a shift of the tube walls at the break site can be achieved.

In preferred embodiment, the holding element of the medical device according to the invention is at least partially wider for stabilization of a patient's limb, especially in a joint area of the patient's limb. The wider portion of the holding element also distributes the pressure applied by the body, thus increasing comfort of the patient. Preferably the holding element is a strip.

The body of the medical device is preferably made of transparent material. Also preferably the holding element is made of transparent material.

As an additional preferred feature, the device is at least partially coated with antibacterial coating or with coagulating agent coating. The said coating is especially preferred in the first compression area or, if the device of the invention is equipped with the elastic pad, on said elastic pad.

In the preferred embodiment the body and the holding element are made of plastic material.

Also preferably the medical device of the invention is sterile.

In the best mode, the body of the device according to the invention has a tube-like shape with beveled endings, which is made of transparent plastic material; the holding element is a strip made of transparent plastic material; the second compression area is situated on the outer surface of the body on the opposite side of the body with respect to the first compression area; the third compression area adapted to be pressed manually with a thumb is situated inside the body; and the fastening means is a hook and loop fastener. Preferably the elastic pad is attached to the first compression area.

The invention also provides a method of achieving local hemostasis of the selected blood vessel at a patient's limb, while maintaining blood flow through other blood vessels in the proximity of said selected blood vessel, wherein the medical device of the invention is applied at a bleeding vessel site by pressing manually the body against the bleeding vessel site followed by immobilizing the body on the patient's limb by applying the holding element around the patient's limb and fixing the holding element by the fastening means. Preferably, the method of the invention is used at the blood vessel from which a catheter or a cannula is being removed, more preferably the vessel is an artery, and most preferably a radial artery.

The invention also provides a method for stopping bleeding from a wound on patient's limb, wherein the medical device of the invention is applied at a wound site by pressing manually the body against the wound site followed by immobilizing the body on the patient's limb by applying the holding element around the patient's limb and fixing the holding element by the fastening means.

The invention provides further the use of the medical device according to the invention for achieving local hemostasis of the selected blood vessel at a patient's limb, preferably a radial artery.

Provided herein is also the use of the medical device according to the invention for stopping bleeding at a patient's limb.

The medical device according to the invention facilitates the work of the medical staff and ensures proper haemostasis following procedures that require an arterial vascular access port. The device is simple and user-friendly both for the patient and the medical staff.

DESCRIPTION OF THE DRAWING

The present invention will be described in a greater detail herein below in reference to a drawing wherein.

DESCRIPTION OF PREFERRED EMBODIMENTS

Figure 1:
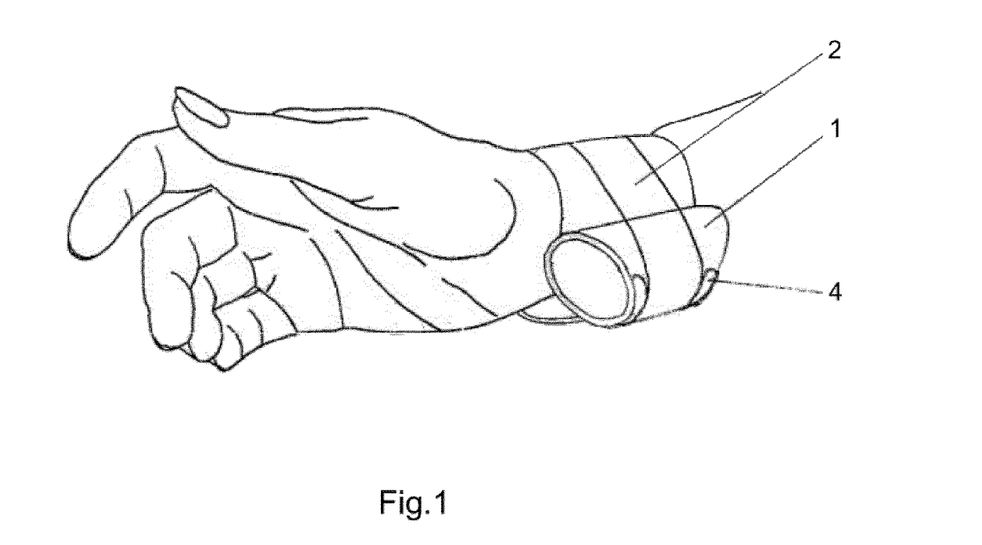
FIG. 1 presents a general bottom view of the device fastened on a forearm in the proximity of the wrist is presented.
Figure 2:
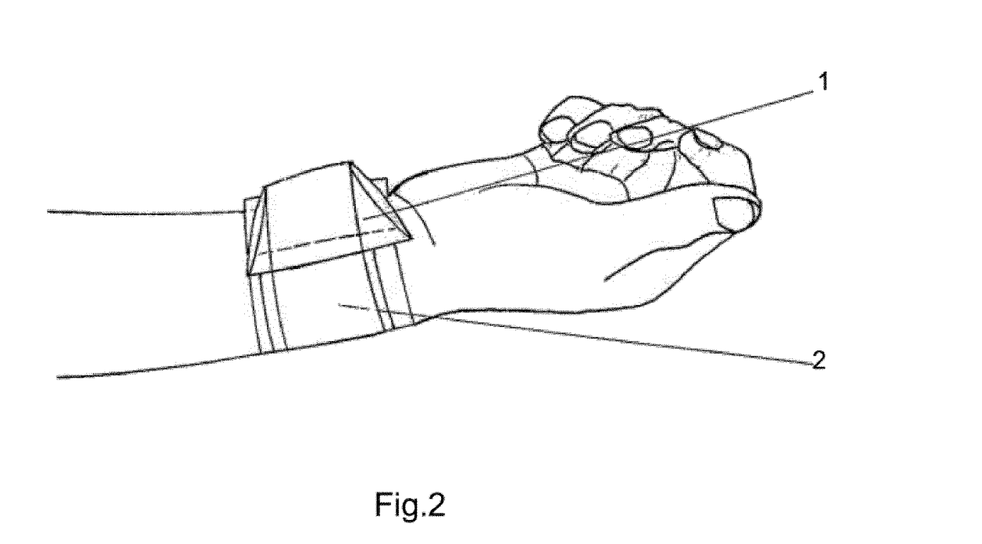
FIG. 2 presents a general view of the device fastened on a forearm in the proximity of the wrist from the side of the radial artery.
Figures 3, 4:
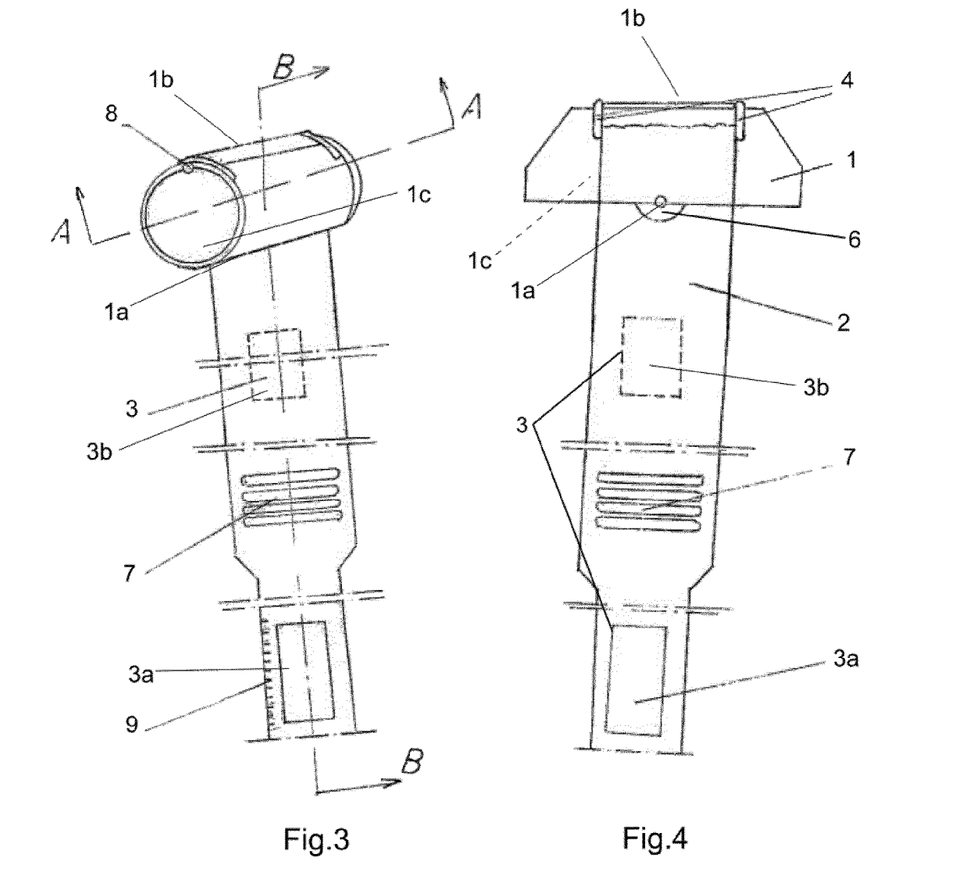
FIG. 3 shows a perspective view of the device having a hollow body.
FIG. 4 presents a side view of the device having the hollow body and bevelled endings.

In FIG. 1 the first preferred embodiment of the medical device of the invention is shown, fastened on the forearm in the proximity of the wrist above the radial artery ra and opposite the ulnar artery ua. The device comprises a body 1, made of a transparent material, shaped as a hollow cylinder bevelled at both ends. To the outer surface of the body 1 a holding element 2 is attached in a form of the transparent strip. The body 1 is equipped with two guiding means 4 that guide the strip in an appropriate position over the body 1 when the device is applied to the patient's limb. The strip is wrapped around the patient's limb and the body 1 is fastened at an appropriate position. The position of the strap ensures that the required compression force is applied to the patient's limb at the contact site.

A more detailed view of the first preferred embodiment of the device is presented in FIG. 3, FIG. 4, FIG. 5 and FIG. 6, wherein the body 1 has the first compression area 1*a*, the second compression area 1*b* and the third compression area 1*c*. The first compression area 1*a* applies the compression force to the blood vessel at the contact site and is situated at the outer surface of the body 1. The second compression area 1*b* is also situated at the outer surface of the body 1, however on the opposite side of the body 1 relative to the first compression area 1*a*. The third compression area 1*c* is located inside the body 1. In this embodiment the second compression area 1*b* is located above the third compression area 1*c*.

Figure 5:
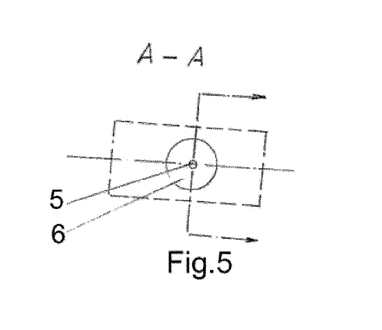
FIG. 5 shows a cross-section A-A of the body of the device of FIG. 1.
Figure 6:
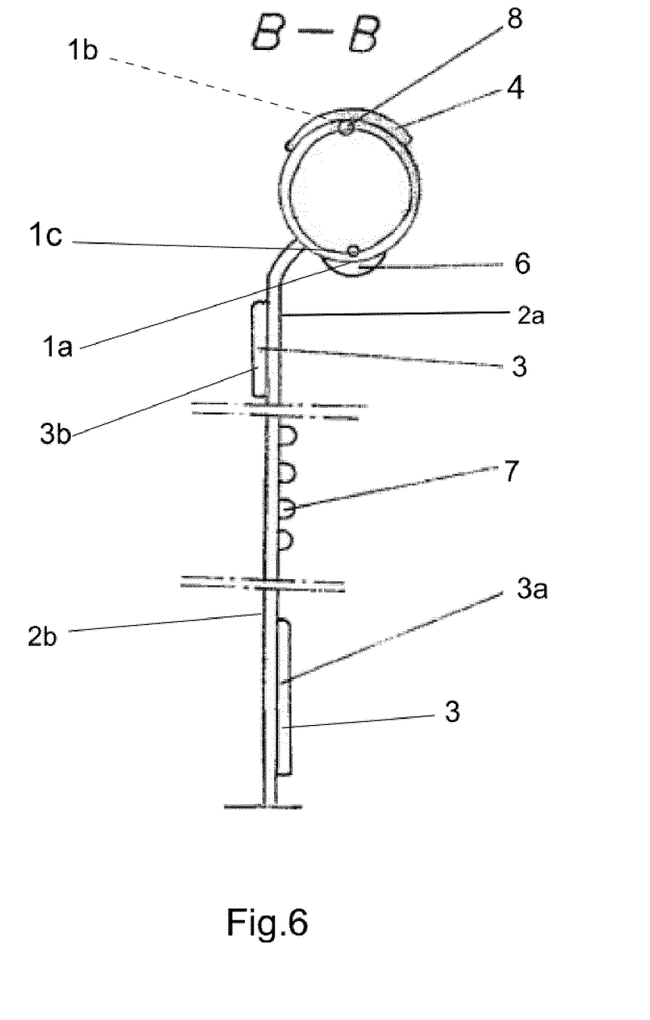
FIG. 6 shows a longitudinal section B-B of the device of FIG. 1.

The strip has an inner surface 2*a* for contacting at least partially with a patient's limb and an outer surface 2*b* situated on the opposite side of the strip. The fastening means 3 on the strip is a hook and loop fastener. The hook and loop fastener consists of the first part 3*a* and the second part 3*b*. The first part 3*a*, which is a loop part of the hook and loop fastener, is located on the inner surface 2*a* of the strip. The second part 3*b*, which is a hook part of the hook and loop fastener, is located on the outer surface 2*b*. The holding element 2, which is a strip, is widened in the area corresponding to the back of the wrist. When applied to the limb at the bleeding vessel or wound site the strip is placed between the guiding means 4 located on the outer surface of the body 1, at a site corresponding to the second compression area 1*b*. The guiding means 4 prevents the holding element 2 from sliding to the sides over the surface of the body 1. FIG. 5 presents a cross section of the body 1, where the insertion site mark 5 and the elastic pad 6 are shown. The insertion site mark 5 represents a site of the body 1, that is contacted with the bleeding vessel site on the patient's limb. Around the insertion site mark 5, an elastic pad 6 is attached to the outer surface of the body 1. The elastic pad 6 on the side adjacent to the patient's limb is coated with a blood coagulating agent.

Figure 11:
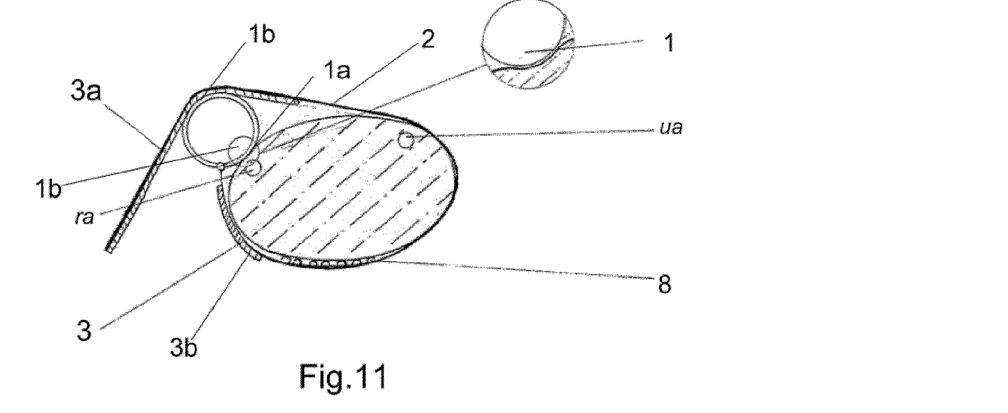
FIG. 11 presents a cross section of the device of FIG. 1 on a wrist, together with a detail presenting the contact site of the body with the patient's limb.

The holding element 2 is equipped with protrusions 7, which optimize the pressure exerted on the opposite side of the patient's limb relative to the site where body is pressed against the limb and improve the patient's comfort. The protrusions 7 are situated on the inner surface 2*a* of the strip, between part 3*a* and 3*b* of the hook and loop fastener. In the narrowed part of the holding element 2, there is a scale 9 which together with the marker 8 on the body 1 provides means for controlling compression force of the medical device. FIG. 11 presents a cross section of the device in the first preferred embodiment on the wrist of the patient. The device is designed in such a way that no compression is exerted on the ulnar nerve and artery ua.

Figure 7:
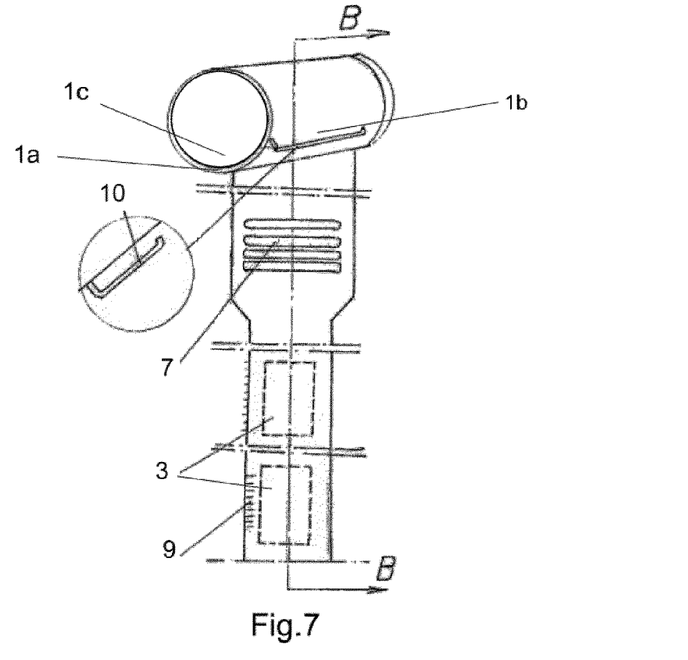
FIG. 7 presents a perspective view of the device having the hollow body and a hook as a tracking element.
Figure 8:
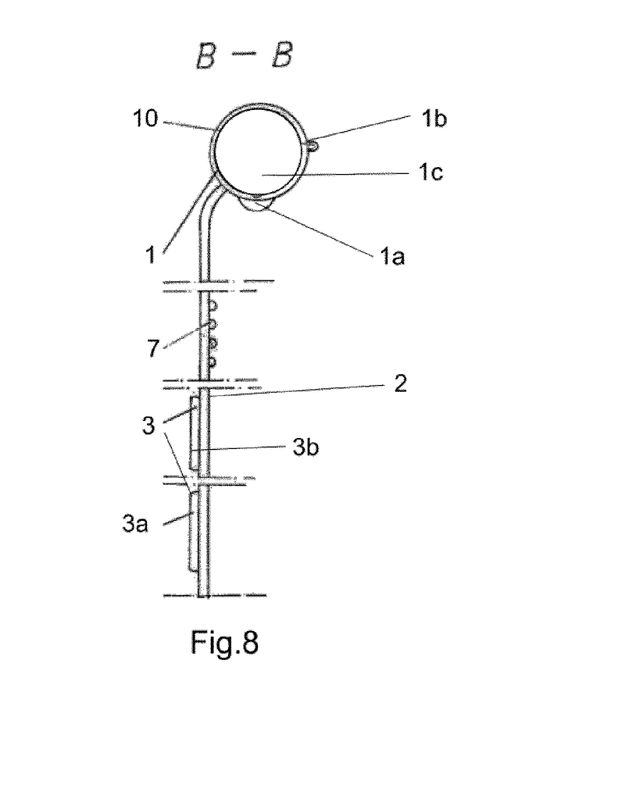
FIG. 8 shows a longitudinal section B-B of the device of FIG. 7
Figure 12:
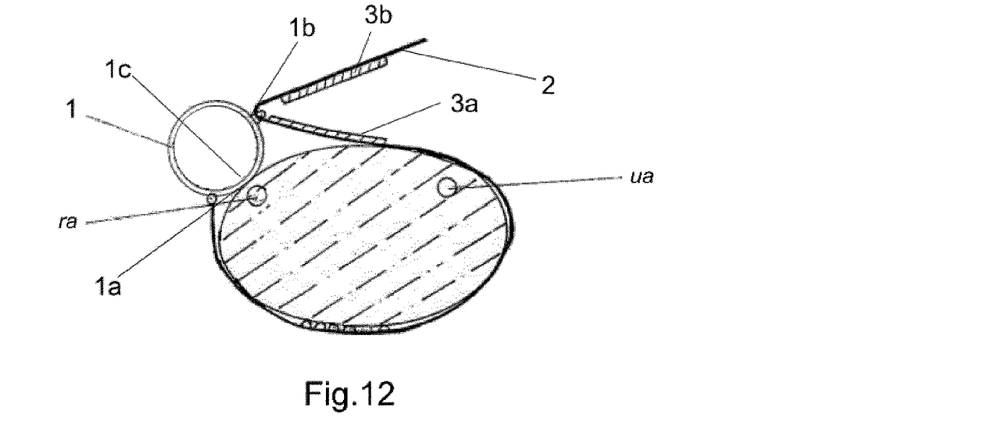
FIG. 12 shows a cross section of the device of FIG. 7 on a wrist.

FIG. 7 and FIG. 8 present the second preferred embodiment. The medical device of the second preferred embodiment differs from the device presented in the first preferred embodiment in that instead of guiding means 4, the body 1 is equipped with the anchoring element 10 in a form of a hook for hooking up the holding element 2 in the form of a strip. Moreover, both the first part 3*a* and the second part 3*b* of the hook and loop fastener are located on the outer surface 2*b* of the holding element 2. In the second embodiment the holding element 2 is wrapped around the patient limb, however it is not guided over the body 1. Instead the strip is guided through the anchoring element 10 back in the direction of the patient's limb and fastened by attaching the first part 3*a* of the hook and loop fastener to the second part 3*b* of the hook and loop fastener. In this embodiment no marker 8 on the body 1 is necessary to control the compression force. The compression force can be adjusted by using scale 9 located on the holding element 2. FIG. 12 presents a cross section of the device of the second preferred embodiment on the wrist of the patient. The use of the anchoring element 10 ensures that the strip is guided above the area of the ulnar nerve and artery, thus preventing it from being pressed.

Figure 9:
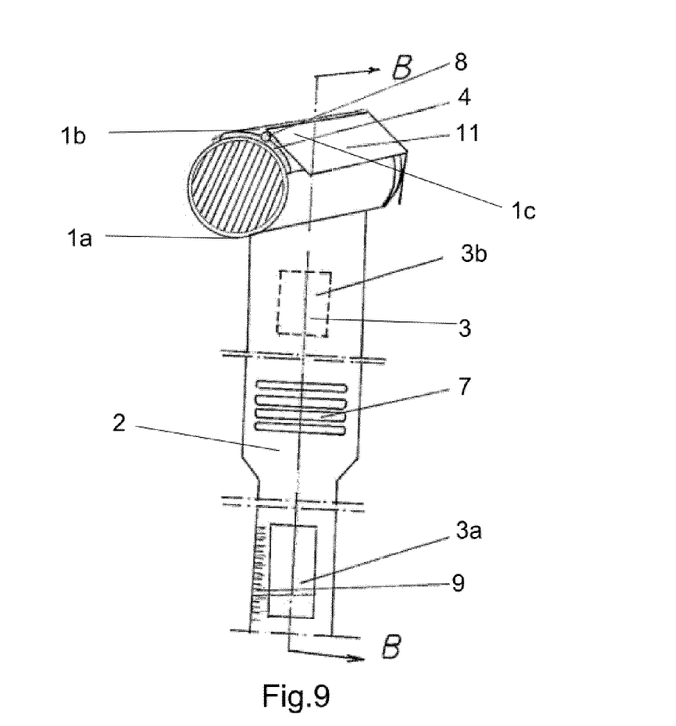
FIG. 9 presents a perspective view of the device with a solid body.
Figure 10:
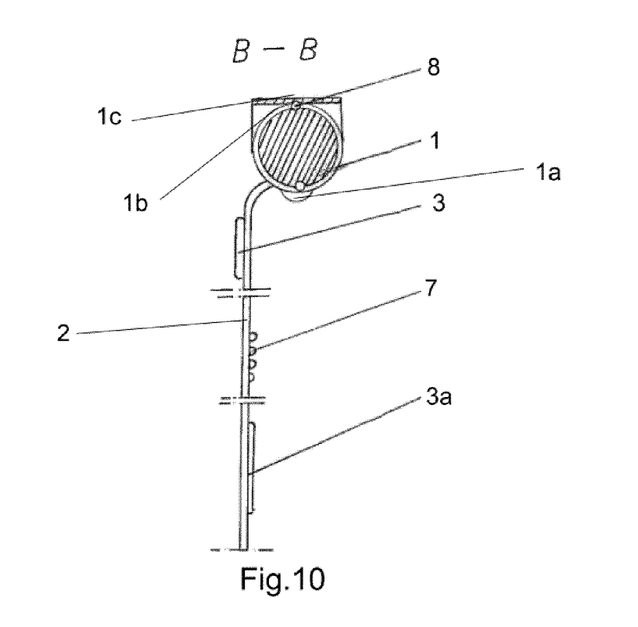
FIG. 10 shows a longitudinal section B-B of the device of FIG. 9.
Figure 13:
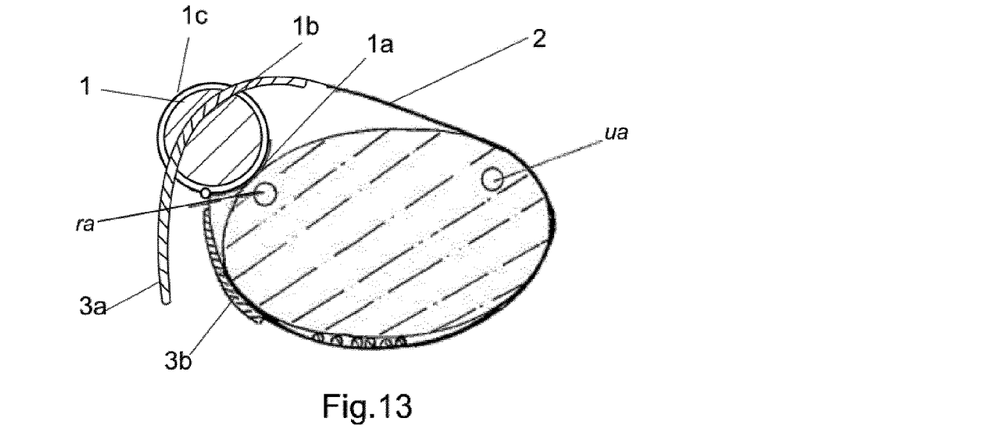
FIG. 13 presents a cross section of the device of FIG. 9 on a wrist.
Figure 14A:
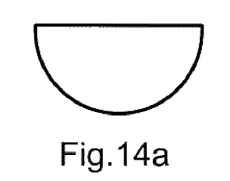
FIG. 14a-14d present cross sections for selected shapes of the body of the device according to the invention.
Figure 14B:
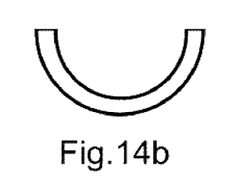
Figure 14C:
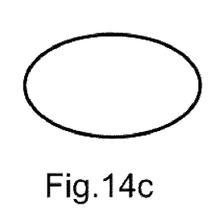
Figure 14D:
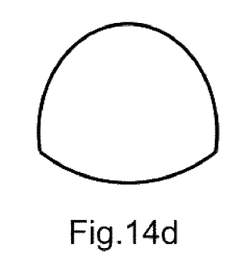

FIG. 9 and FIG. 10 present the third preferred embodiment, which differs from the first preferred embodiment in that the body 1 is a solid cylinder and that instead of guiding means 4 comprises the tracking element 11. In the third preferred embodiment the holding element 2 is wrapped around the patient limb and guided through the tracking element of the body 1 to the other side of the body, where the first part 3*a* of the hook and loop fastener situated on the inner surface 2*a* of the strap is attached to the second part 3*b* of the hook and loop fastener situated on the outer surface 2*b* of the strap. In this embodiment the third compression area 1*c* is situated over the second compression area 1*b*. FIG. 13 presents a cross section of the device of the third preferred embodiment on the wrist of the patient. Also in this embodiment the holding element 2 is guided above the area of the ulnar nerve and artery when device is applied to the patient's limb.

In other preferred embodiments the body 1 is elongated, however has a shape that differs from those described above. FIG. 14*a-d* present preferred shapes of the body 1 cross sections.

Figure 15A:
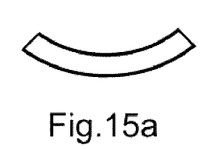
FIG. 15a-15c present cross sections for selected shapes of the pad situated on the body of the device according to the invention.
Figure 15B:
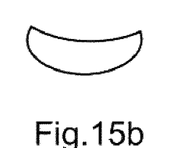
Figure 15C:
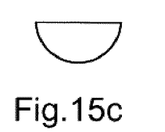

Also the preferred shapes of the elastic pad 6 cross sections are illustrated in FIG. 15*a-c*.

Figure 16A:
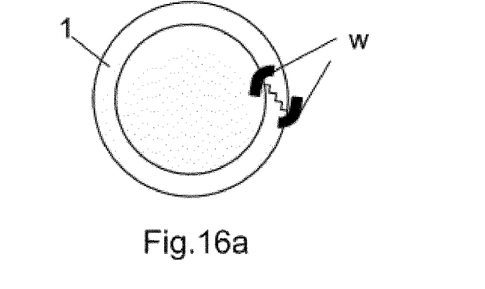
FIG. 16a-16e present cross sections of the body equipped with adjusting means for adjusting dimensions of the body.
Figure 16B:
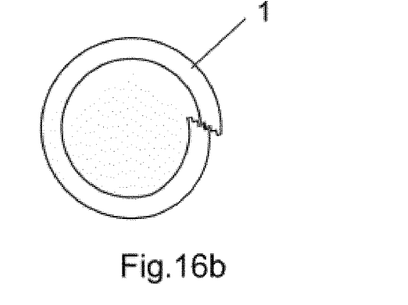
Figure 16C:
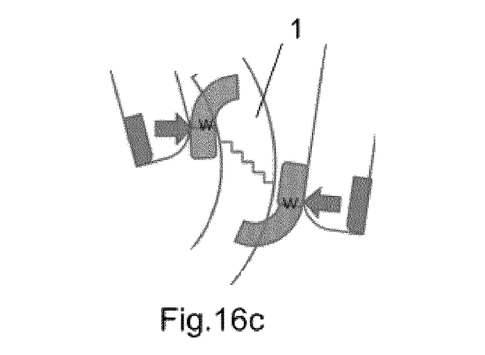
Figure 16D:
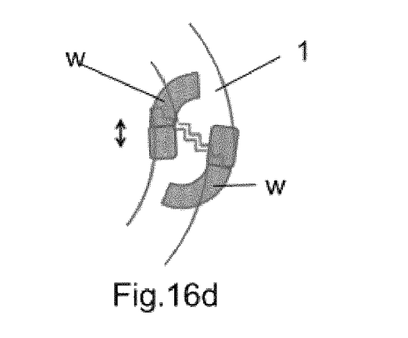
Figure 16E:
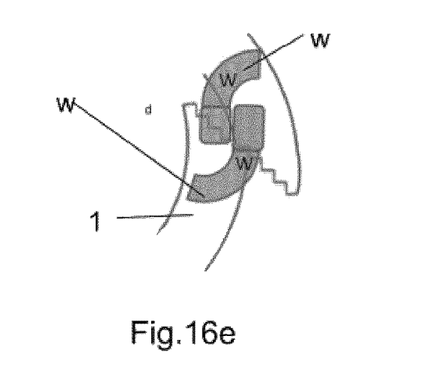
Figure 16F:
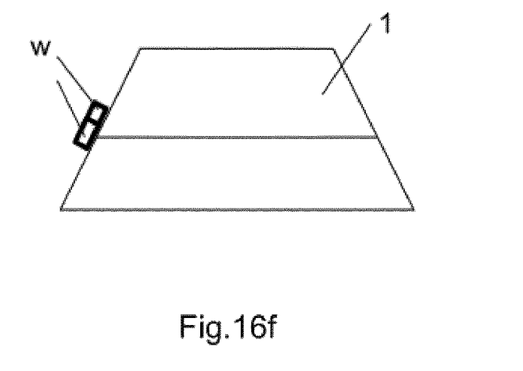
FIG. 16f presents a side view of the body equipped with adjusting means for adjusting dimensions of the body.

In a particularly preferred embodiment a cross-section size of the body 1 is adjustable for controlling the compression force applied to the blood vessel. This adjustment of the cross-section of the body 1 is preferably implemented by a disruption in the surface area of the body 1 as presented in FIG. 16*a-f*. A body 1 has a shape of a tube and to control the dimension of the body 1 a disruption in the longitudinal direction of the tube is used. By pressing the walls of the tube in one direction the dimension of the cross section of the tube is decreased and by pressing the walls in the opposite direction the dimension of the cross section of the tube is increased. The disruption in the tube wall is equipped with a rack/teeth element 12, which is in the shape of leaned sawteeth. By pressing the tube wall at the disruption site (as shown in FIG. 16*d*), one part of the wall is shifted relatively to the other. The shift of the tube walls at the disruption site is blocked with by winglets W (as shown in FIG. 16*d*). When the parts of the ring are in the extreme shift, further movement is prevented by the winglets W, which are pressing against each other (as shown in FIG. 16*e*).

Figure 17A:
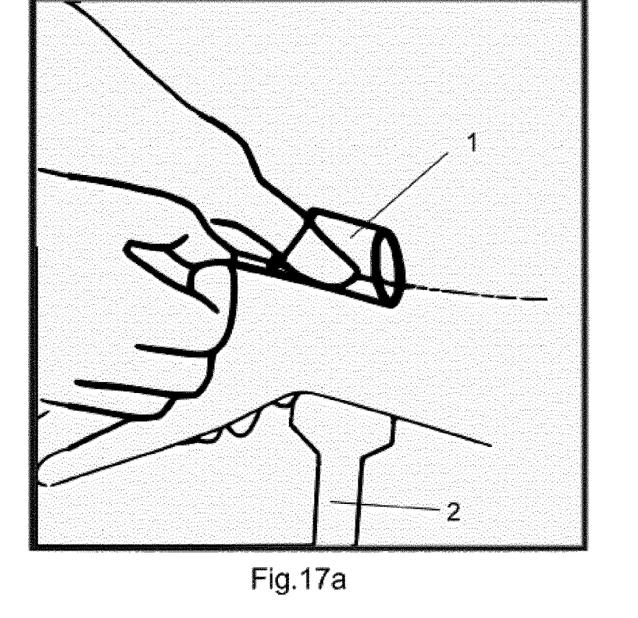
FIG. 17a-17b shows how the medical device of the invention is applied on the patient's limb.
Figure 17B:
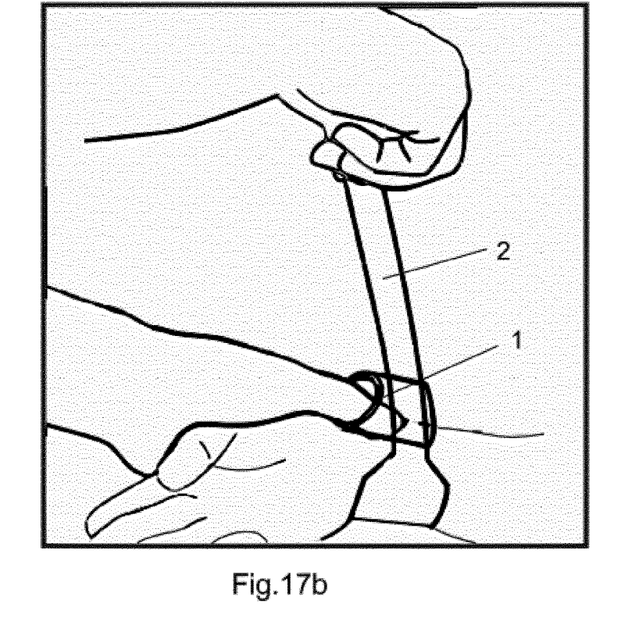

FIG. 17*a-b* present the preferred embodiment of the methods of the invention. When the device of the invention is applied to the patient's limb, the body 1 is initially held with the thumb in the third compression area 1*c* as shown in FIG. 17*a*. The appropriate compression force is adjusted manually with the thumb, when other activities such as the removal of the vascular sheath are performed. Subsequently the holding element 2, which is a strip, is wrapped around the forearm in the proximity of the wrist and the body 1 as shown in FIG. 17b. The strip is positioned over the body 1 between the guiding elements 4. The strip when positioned over the body 1 exerts pressure against the second compression area 1b. The device is fastened when the first part 3a of the hook and loop fastener is attached to the other part 3b of the hook and loop fastener. Once the device is held in the desirable position and the appropriate compression is applied the thumb is released

The invention claimed is:

1. A medical device comprising:
    a body for blood vessel compression, said body comprising an elongated cylindrical tube which is hollow and open-ended, and wherein endings of the body are beveled,
    a holding element—for attaching the body to a patient's limb at a contact site of the body with the patient's limb by wrapping the holding element around the patient's limb and the body at least once,
    a fastening means situated on the holding element for holding the device in a desirable position on the patient's limb,
    wherein the body comprises:
    a first compression area for applying the compression force to the blood vessel at the contact site situated within the first compression area, said first compression area being situated at the outer surface of the body,
    at least one second compression area through which the body is pressed with the holding element against patient's limb, and
    a third compression area adapted to be pressed manually for compression control during application of the device onto the patient's limb, wherein said third compression area being situated inside the body, and
    wherein the holding element is attached to the body in the proximity of the first compression area.

2. The medical device of claim 1, wherein the first compression area has a convex shape.

3. The medical device of claim 1, wherein a longitudinal cross section of the body is a rectangle and a transverse cross section of the body is a circle.

4. The medical device of claim 1, wherein the third compression area is configured to be pressed with a thumb.

5. The medical device of claim 1, wherein the distance between the first compression area and the third compression area is smaller than the distance between the first compression area and the second compression area.

6. The medical device of claim 1, wherein the distance between the first compression area and the second compression area is smaller than the distance between the first compression area and the third compression area.

7. The medical device of claim 1, wherein an elastic pad is attached to the first compression area.

8. The medical device of claim 7, wherein the elastic pad is detachably attached for exchanging the pad.

9. The medical device of claim 7, wherein the elastic pad is made of a heat activated material.

10. The medical device of claim 9, wherein the elastic pad is made of a heat activated material that softens at the body temperature.

11. The medical device of claim 7, wherein the elastic pad is made of rubber, silicon or foam materials.

12. The medical device of claim 1, wherein the holding element has an inner surface for contacting at least partially with a patient's limb and an outer surface situated on the opposite side of the holding element.

13. The medical device of claim 12, wherein the inner surface of the holding element is coated with non-skid layer.

14. The medical device of claim 12, wherein the inner surface of the holding element is equipped, at least partially, with protrusions.

15. The medical device of claim 12, wherein the inner surface of the holding element is equipped, at least partially, with openings.

16. The medical device of claim 12, wherein the inner surface of the holding element is equipped, at least partially, with recesses.

17. The medical device of claim 1, wherein the fastening means consists of a first part and a second part, wherein the first part of the fastening means is situated on the inner surface of the holding element and the second part of the fastening means is situated on the outer surface of the holding element.

18. The medical device of claim 17, wherein the fastening means is a hook and loop fastener.

19. The medical device of claim 17, wherein the fastener is a buckle, preferably a tightening buckle.

20. The medical device of claim 1, wherein the holding element is made of a non-skid material.

21. The medical device of claim 1, wherein the body is equipped with at least one guiding means for positioning the holding element.

22. The medical device of claim 1, wherein the holding element has a scale for indicating a position of the holding element for controlling compression force applied to the blood vessel.

23. The medical device of claim 1, wherein the body is equipped with adjusting means for adjusting dimensions of the body to control the compression force applied to the blood vessel.

24. The medical device of claim 23, wherein a cross-section size of the body is adjustable for controlling the compression force applied to the blood vessel.

25. The medical device of claim 1, wherein one section of the holding element is wider than the rest of the holding element for stabilization of a patient's limb, especially in a joint area of the patient's limb.

26. The medical device of claim 1, wherein the holding element is a strip.

27. The medical device of claim 1, wherein the body is made of transparent material.

28. The medical device of claim 1, wherein the holding element is made of transparent material.

29. The medical device of claim 1, wherein the device is at least partially coated with antibacterial coating.

30. The medical device of claim 1, wherein the device is at least partially coated with coagulating agent coating.

31. The medical device of claim 1, wherein the body and the holding element are made of plastic material.

32. The medical device of claim 1, wherein the device is sterile.

33. A method of achieving local hemostasis of the selected blood vessel at a patient's limb, while maintaining blood flow through other blood vessels in the proximity of said selected blood vessel, wherein the medical device of claim 1 is applied at a bleeding vessel site by pressing manually the third compression area located within the body against the bleeding vessel site followed by immobilizing the body on the patient's limb and over the body to exert pressure against the second compression area by applying the holding element around the patient's limb and fixing the holding element by the fastening means.

34. The method of claim 33, wherein the blood vessel is a vessel from which a catheter or a cannula is being removed.

35. The method of claim 34, wherein the vessel is an artery.

36. The method of claim 35, wherein the artery is a radial artery.

37. The method of claim 35, wherein the artery is a femoral artery.

* * * * *